United States Patent
Wang et al.

(10) Patent No.: US 12,398,210 B2
(45) Date of Patent: Aug. 26, 2025

(54) B7-H3 NANOBODY, PREPARATION METHOD AND USE THEREOF

(71) Applicants: Dartsbio Pharmaceuticals Ltd., Zhongshan (CN); Shanghai Mabstone Biotechnology Ltd., Shanghai (CN); Shenzhen Innovastone Biopharma Ltd., Guangdong (CN)

(72) Inventors: Chunhe Wang, Zhongshan (CN); Yi-li Chen, Zhongshan (CN); Xinyuan Liu, Zhongshan (CN); Weidong Luo, Zhongshan (CN); Guojian Liu, Zhongshan (CN); Huanhuan Li, Zhongshan (CN); Yijun Lin, Zhongshan (CN)

(73) Assignees: DARTSBIO PHARMACEUTICALS LTD., Zhongshan (CN); SHANGHAI MABSTONE BIOTECHNOLOGY LTD., Shanghai (CN); SHENZHEN INNOVASTONE BIOPHARMA LTD., Shenzhen (CN)

( * ) Notice: Subject to any disclaimer, the term of this patent is extended or adjusted under 35 U.S.C. 154(b) by 449 days.

(21) Appl. No.: 17/767,444

(22) PCT Filed: Oct. 9, 2020

(86) PCT No.: PCT/CN2020/119893
§ 371 (c)(1),
(2) Date: Apr. 8, 2022

(87) PCT Pub. No.: WO2021/068871
PCT Pub. Date: Apr. 15, 2021

(65) Prior Publication Data
US 2024/0092910 A1    Mar. 21, 2024

(30) Foreign Application Priority Data
Oct. 9, 2019 (CN) .......................... 201910953967.4

(51) Int. Cl.
*C07K 16/28* (2006.01)

(52) U.S. Cl.
CPC ...... *C07K 16/2827* (2013.01); *C07K 2317/22* (2013.01); *C07K 2317/569* (2013.01); *C07K 2317/76* (2013.01)

(58) Field of Classification Search
CPC combination set(s) only.
See application file for complete search history.

(56) References Cited

U.S. PATENT DOCUMENTS

| 9,790,282 B2 | 10/2017 | Orentas et al. |
| 2013/0078234 A1 | 3/2013 | Takahashi et al. |
| 2017/0073416 A1 | 3/2017 | Couto et al. |

FOREIGN PATENT DOCUMENTS

| CN | 101104639 A | 1/2008 |
| CN | 103687945 A | 3/2014 |
| CN | 110305213 A | 10/2019 |
| CN | 110642948 A | 1/2020 |
| WO | 2015/181267 A1 | 12/2015 |
| WO | 2018/161872 A1 | 9/2018 |

OTHER PUBLICATIONS

Extended European Search Report issued Nov. 8, 2022 in corresponding European Patent Application No. 20875295.6, 9 pages.
Serge Muyldermans, "Nanobodies: Natural Single-Domain Antibodies", Annual Review of Biochemistry, vol. 82, No. 1, Jun. 2, 2013, pp. 775-797, 26 pages.
International Search Report and Written Opinion mailed on Jan. 15, 2021, received for PCT Application PCT/CN2020/119893, Filed on Oct. 9, 2020, 19 pages including English Translation.

*Primary Examiner* — Misook Yu
*Assistant Examiner* — James Lyle McLellan
(74) *Attorney, Agent, or Firm* — XSENSUS LLP

(57) ABSTRACT

The present invention provides a B7-H3 nanobody, the preparation method and use thereof. The B7-H3 nanobody comprises framework regions 1-4 (FR 1-4) and complementarity determining regions 1-3 (CDR 1-3), can specifically bind to B7-H3, and can be used for detecting B7-H3 molecules, and be used for the treatment of various malignant tumors with abnormal expression of B7-H3 molecule.

7 Claims, 1 Drawing Sheet
Specification includes a Sequence Listing.

```
                        SEQUENCE LISTING

<160> NUMBER OF SEQ ID NOS: 96

<210> SEQ ID NO 1
<211> LENGTH: 30
<212> TYPE: PRT
<213> ORGANISM: artificial sequence
<220> FEATURE:
<223> OTHER INFORMATION: FR1

<400> SEQUENCE: 1

Asp Val Gln Leu Gln Glu Ser Gly Gly Gly Ser Val Gln Ala Gly Gly
1               5                   10                  15

Ser Leu Arg Leu Ser Cys Ala Ala Ser Gly Val Ala His Arg
            20                  25                  30

<210> SEQ ID NO 2
<211> LENGTH: 14
<212> TYPE: PRT
<213> ORGANISM: artificial sequence
<220> FEATURE:
<223> OTHER INFORMATION: FR2

<400> SEQUENCE: 2

Trp Phe Arg Gln Ala Pro Gly Lys Glu Arg Glu Gly Val Ala
1               5                   10

<210> SEQ ID NO 3
<211> LENGTH: 32
<212> TYPE: PRT
<213> ORGANISM: artificial sequence
<220> FEATURE:
<223> OTHER INFORMATION: FR3

<400> SEQUENCE: 3

Arg Phe Thr Ile Ser Gln Asp Asn Ala Asn Asp Met Val Tyr Leu Gln
1               5                   10                  15

Met Leu Ser Leu Lys Pro Glu Asp Thr Ala Met Tyr Tyr Cys Ala Ala
            20                  25                  30

<210> SEQ ID NO 4
<211> LENGTH: 11
<212> TYPE: PRT
<213> ORGANISM: artificial sequence
<220> FEATURE:
<223> OTHER INFORMATION: FR4

<400> SEQUENCE: 4

Trp Gly Gln Gly Thr Gln Val Thr Val Ser Ser
1               5                   10

<210> SEQ ID NO 5
<211> LENGTH: 5
<212> TYPE: PRT
<213> ORGANISM: artificial sequence
<220> FEATURE:
<223> OTHER INFORMATION: CDR1

<400> SEQUENCE: 5

Arg Tyr Tyr Met Ser
1               5

<210> SEQ ID NO 6
<211> LENGTH: 17
```

```
<212> TYPE: PRT
<213> ORGANISM: artificial sequence
<220> FEATURE:
<223> OTHER INFORMATION: CDR2

<400> SEQUENCE: 6

Ser Ile Tyr Ile Gly Ser Gly Ser Thr Asp Tyr Val Asp Ser Val Lys
1               5                   10                  15
Gly

<210> SEQ ID NO 7
<211> LENGTH: 14
<212> TYPE: PRT
<213> ORGANISM: artificial sequence
<220> FEATURE:
<223> OTHER INFORMATION: CDR3

<400> SEQUENCE: 7

Gly Leu Tyr Gly Gly Arg Trp Asp Arg Ala Gln Tyr Lys Tyr
1               5                   10

<210> SEQ ID NO 8
<211> LENGTH: 30
<212> TYPE: PRT
<213> ORGANISM: artificial sequence
<220> FEATURE:
<223> OTHER INFORMATION: FR1

<400> SEQUENCE: 8

Asp Val Gln Leu Gln Glu Ser Gly Gly Gly Ser Val Gln Ala Gly Gly
1               5                   10                  15
Ser Leu Arg Leu Ser Cys Thr Ala Ser Gly Tyr Thr Arg Ser
            20                  25                  30

<210> SEQ ID NO 9
<211> LENGTH: 15
<212> TYPE: PRT
<213> ORGANISM: artificial sequence
<220> FEATURE:
<223> OTHER INFORMATION: FR2

<400> SEQUENCE: 9

Trp Phe Arg Gln Ala Pro Gly Lys Glu Arg Glu Gly Val Ala Ala
1               5                   10                  15

<210> SEQ ID NO 10
<211> LENGTH: 35
<212> TYPE: PRT
<213> ORGANISM: artificial sequence
<220> FEATURE:
<223> OTHER INFORMATION: FR3

<400> SEQUENCE: 10

Arg Phe Thr Ile Ser Gln Asp Asn Ala Lys Asn Ala Lys Asn Thr Val
1               5                   10                  15
Tyr Leu Gln Met Asn Ser Leu Lys Pro Glu Asp Thr Ala Met Tyr Tyr
            20                  25                  30
Cys Ala Ala
        35

<210> SEQ ID NO 11
<211> LENGTH: 11
<212> TYPE: PRT
<213> ORGANISM: artificial sequence
<220> FEATURE:
```

```
<223> OTHER INFORMATION: FR4

<400> SEQUENCE: 11

Trp Gly Gln Gly Thr Gln Val Thr Val Ser Ser
1               5                   10

<210> SEQ ID NO 12
<211> LENGTH: 5
<212> TYPE: PRT
<213> ORGANISM: artificial sequence
<220> FEATURE:
<223> OTHER INFORMATION: CDR1

<400> SEQUENCE: 12

Thr Ile Trp Ile Gly
1               5

<210> SEQ ID NO 13
<211> LENGTH: 16
<212> TYPE: PRT
<213> ORGANISM: artificial sequence
<220> FEATURE:
<223> OTHER INFORMATION: CDR2

<400> SEQUENCE: 13

Ile Tyr Ile Gly Ser Gly Ala Thr Tyr Tyr Val Asp Ser Val Lys Gly
1               5                   10                  15

<210> SEQ ID NO 14
<211> LENGTH: 19
<212> TYPE: PRT
<213> ORGANISM: artificial sequence
<220> FEATURE:
<223> OTHER INFORMATION: CDR3

<400> SEQUENCE: 14

Thr Gly Gly Thr Val Gly Ser Met Val Arg Phe Ser Pro Val Gly Asp
1               5                   10                  15

Phe Gly Tyr

<210> SEQ ID NO 15
<211> LENGTH: 30
<212> TYPE: PRT
<213> ORGANISM: artificial sequence
<220> FEATURE:
<223> OTHER INFORMATION: FR1

<400> SEQUENCE: 15

Asp Val Gln Leu Gln Glu Ser Gly Gly Gly Leu Val Gln Pro Gly Gly
1               5                   10                  15

Ser Leu Arg Leu Ser Cys Ala Ala Ser Gly Phe Thr Phe Thr
            20                  25                  30

<210> SEQ ID NO 16
<211> LENGTH: 14
<212> TYPE: PRT
<213> ORGANISM: artificial sequence
<220> FEATURE:
<223> OTHER INFORMATION: FR2

<400> SEQUENCE: 16

Trp Val Arg Gln Ala Pro Gly Lys Gly Leu Glu Trp Val Ser
1               5                   10

<210> SEQ ID NO 17
```

<211> LENGTH: 32
<212> TYPE: PRT
<213> ORGANISM: artificial sequence
<220> FEATURE:
<223> OTHER INFORMATION: FR3

<400> SEQUENCE: 17

Arg Ser Thr Ile Ser Arg Asp Asn Ala Lys Asn Thr Leu Tyr Leu Gln
1               5                   10                  15
Leu Asn Ser Leu Glu Thr Glu Asp Thr Ala Met Tyr Tyr Cys Ala Lys
            20                  25                  30

<210> SEQ ID NO 18
<211> LENGTH: 11
<212> TYPE: PRT
<213> ORGANISM: artificial sequence
<220> FEATURE:
<223> OTHER INFORMATION: FR4

<400> SEQUENCE: 18

Arg Gly Gln Gly Thr Gln Val Thr Val Ser Ser
1               5                   10

<210> SEQ ID NO 19
<211> LENGTH: 5
<212> TYPE: PRT
<213> ORGANISM: artificial sequence
<220> FEATURE:
<223> OTHER INFORMATION: CDR1

<400> SEQUENCE: 19

Asn Tyr Ala Met Ser
1               5

<210> SEQ ID NO 20
<211> LENGTH: 16
<212> TYPE: PRT
<213> ORGANISM: artificial sequence
<220> FEATURE:
<223> OTHER INFORMATION: CDR2

<400> SEQUENCE: 20

Gly Ile Asn Ser Asp Gly Gly Thr Tyr Tyr Ser Asn Ser Val Lys Gly
1               5                   10                  15

<210> SEQ ID NO 21
<211> LENGTH: 15
<212> TYPE: PRT
<213> ORGANISM: artificial sequence
<220> FEATURE:
<223> OTHER INFORMATION: CDR3

<400> SEQUENCE: 21

Gly Asn Gly Pro Ser Trp Thr Leu Gly Ser Val Asp Val Asn Ser
1               5                   10                  15

<210> SEQ ID NO 22
<211> LENGTH: 30
<212> TYPE: PRT
<213> ORGANISM: artificial sequence
<220> FEATURE:
<223> OTHER INFORMATION: FR1

<400> SEQUENCE: 22

Asp Val Gln Leu Gln Glu Ser Gly Gly Gly Ser Val Gln Ala Gly Gly
1               5                   10                  15

```
Ser Leu Arg Leu Ser Cys Ala Ala Ser Gly Asp Thr Tyr Arg
            20                  25                  30

<210> SEQ ID NO 23
<211> LENGTH: 32
<212> TYPE: PRT
<213> ORGANISM: artificial sequence
<220> FEATURE:
<223> OTHER INFORMATION: FR3

<400> SEQUENCE: 23

Arg Phe Thr Ile Ser Gln Asp Ser Ala Lys Asn Thr Val Tyr Leu Gln
1               5                   10                  15

Met Asn Ser Leu Lys Pro Glu Asp Thr Ala Ile Tyr Tyr Cys Ala Ala
            20                  25                  30

<210> SEQ ID NO 24
<211> LENGTH: 5
<212> TYPE: PRT
<213> ORGANISM: artificial sequence
<220> FEATURE:
<223> OTHER INFORMATION: CDR1

<400> SEQUENCE: 24

Arg Asn Thr Met Gly
1               5

<210> SEQ ID NO 25
<211> LENGTH: 17
<212> TYPE: PRT
<213> ORGANISM: artificial sequence
<220> FEATURE:
<223> OTHER INFORMATION: CDR2

<400> SEQUENCE: 25

Ala Ile Tyr Thr Gly Gly Thr Ser Thr Ala Tyr Ala Asp Ser Val Arg
1               5                   10                  15

Gly

<210> SEQ ID NO 26
<211> LENGTH: 17
<212> TYPE: PRT
<213> ORGANISM: artificial sequence
<220> FEATURE:
<223> OTHER INFORMATION: CDR3

<400> SEQUENCE: 26

Gly Ser Val Trp Ser Arg Tyr Thr Trp Ser Trp Pro Ser Thr Tyr Ser
1               5                   10                  15

Tyr

<210> SEQ ID NO 27
<211> LENGTH: 30
<212> TYPE: PRT
<213> ORGANISM: artificial sequence
<220> FEATURE:
<223> OTHER INFORMATION: FR1

<400> SEQUENCE: 27

Asp Val Gln Leu Gln Glu Ser Gly Gly Gly Ser Val Gln Ala Gly Gly
1               5                   10                  15

Ser Leu Arg Leu Ser Cys Ala Ala Ser Glu Tyr Ser Tyr Ser
            20                  25                  30
```

```
<210> SEQ ID NO 28
<211> LENGTH: 32
<212> TYPE: PRT
<213> ORGANISM: artificial sequence
<220> FEATURE:
<223> OTHER INFORMATION: FR3

<400> SEQUENCE: 28

Arg Phe Thr Ile Ser Gln Asp Ile Ala Glu Asn Thr Val Tyr Leu Arg
1               5                   10                  15

Met Asn Ser Leu Lys Pro Glu Asp Thr Ala Met Tyr Tyr Cys Ala Ala
            20                  25                  30

<210> SEQ ID NO 29
<211> LENGTH: 5
<212> TYPE: PRT
<213> ORGANISM: artificial sequence
<220> FEATURE:
<223> OTHER INFORMATION: CDR1

<400> SEQUENCE: 29

Arg Lys Trp Met Gly
1               5

<210> SEQ ID NO 30
<211> LENGTH: 16
<212> TYPE: PRT
<213> ORGANISM: artificial sequence
<220> FEATURE:
<223> OTHER INFORMATION: CDR2

<400> SEQUENCE: 30

Ala Ile Tyr Thr Ser Gly Arg Thr Ala Val Ala Asp Ser Val Lys Gly
1               5                   10                  15

<210> SEQ ID NO 31
<211> LENGTH: 16
<212> TYPE: PRT
<213> ORGANISM: artificial sequence
<220> FEATURE:
<223> OTHER INFORMATION: CDR3

<400> SEQUENCE: 31

Leu Thr Gly Ala Ser Asp Ser Pro Leu Arg Pro Ser Glu Tyr Asn Tyr
1               5                   10                  15

<210> SEQ ID NO 32
<211> LENGTH: 30
<212> TYPE: PRT
<213> ORGANISM: artificial sequence
<220> FEATURE:
<223> OTHER INFORMATION: FR1

<400> SEQUENCE: 32

Asp Val Gln Leu Gln Glu Ser Gly Gly Gly Ser Val Gln Ala Gly Gly
1               5                   10                  15

Ser Leu Arg Leu Ser Cys Ala Ala Ser Gly Phe Thr Phe Ser
            20                  25                  30

<210> SEQ ID NO 33
<211> LENGTH: 32
<212> TYPE: PRT
<213> ORGANISM: artificial sequence
<220> FEATURE:
<223> OTHER INFORMATION: FR3

<400> SEQUENCE: 33
```

```
Arg Phe Thr Ile Ser Arg Asp Asn Ala Lys Asn Thr Met Tyr Leu Gln
1               5                   10                  15

Met Asn Ser Leu Lys Pro Glu Asp Thr Ala Met Tyr Tyr Cys Ala Ala
            20                  25                  30

<210> SEQ ID NO 34
<211> LENGTH: 5
<212> TYPE: PRT
<213> ORGANISM: artificial sequence
<220> FEATURE:
<223> OTHER INFORMATION: CDR1

<400> SEQUENCE: 34

Ser Tyr Asp Met Ser
1               5

<210> SEQ ID NO 35
<211> LENGTH: 17
<212> TYPE: PRT
<213> ORGANISM: artificial sequence
<220> FEATURE:
<223> OTHER INFORMATION: CDR2

<400> SEQUENCE: 35

Ala Ile Asn Ser Gly Gly Gly Ser Thr Tyr Tyr Ala Asp Ser Val Lys
1               5                   10                  15

Gly

<210> SEQ ID NO 36
<211> LENGTH: 21
<212> TYPE: PRT
<213> ORGANISM: artificial sequence
<220> FEATURE:
<223> OTHER INFORMATION: CDR3

<400> SEQUENCE: 36

Asp Pro Gly Ser Ser Leu Ala Val Gly Ala Trp Leu Lys Ala Ala Asp
1               5                   10                  15

Pro Phe Tyr Gly Tyr
            20

<210> SEQ ID NO 37
<211> LENGTH: 19
<212> TYPE: PRT
<213> ORGANISM: artificial sequence
<220> FEATURE:
<223> OTHER INFORMATION: CDR3

<400> SEQUENCE: 37

Thr Ser Gly Thr Val Gly Ser Met Val Arg Phe Ser Pro Val Gly Asp
1               5                   10                  15

Phe Gly Tyr

<210> SEQ ID NO 38
<211> LENGTH: 30
<212> TYPE: PRT
<213> ORGANISM: artificial sequence
<220> FEATURE:
<223> OTHER INFORMATION: FR1

<400> SEQUENCE: 38

Asp Val Gln Leu Gln Glu Ser Gly Gly Gly Leu Val Gln Pro Gly Gly
1               5                   10                  15
```

```
Ser Leu Arg Leu Ser Cys Ala Ala Ser Gly Phe Thr Phe Ser
            20                  25                  30
```

<210> SEQ ID NO 39
<211> LENGTH: 14
<212> TYPE: PRT
<213> ORGANISM: artificial sequence
<220> FEATURE:
<223> OTHER INFORMATION: FR2

<400> SEQUENCE: 39

```
Trp Val Arg Gln Ala Pro Gly Arg Gly Leu Glu Trp Val Ser
1               5                   10
```

<210> SEQ ID NO 40
<211> LENGTH: 32
<212> TYPE: PRT
<213> ORGANISM: artificial sequence
<220> FEATURE:
<223> OTHER INFORMATION: FR3

<400> SEQUENCE: 40

```
Arg Phe Thr Ile Ser Arg Asp Asn Ala Lys Lys Met Leu Tyr Leu Gln
1               5                   10                  15

Met Asp Ser Leu Lys Pro Glu Asp Thr Ala Val Tyr Tyr Cys Ala Thr
            20                  25                  30
```

<210> SEQ ID NO 41
<211> LENGTH: 5
<212> TYPE: PRT
<213> ORGANISM: artificial sequence
<220> FEATURE:
<223> OTHER INFORMATION: CDR1

<400> SEQUENCE: 41

```
Gly Val Asp Met Ser
1               5
```

<210> SEQ ID NO 42
<211> LENGTH: 17
<212> TYPE: PRT
<213> ORGANISM: artificial sequence
<220> FEATURE:
<223> OTHER INFORMATION: CDR2

<400> SEQUENCE: 42

```
Gly Phe Gly Ser Gly Gly Glu Ser Pro Ser Tyr Ala Asp Ser Val Lys
1               5                   10                  15

Gly
```

<210> SEQ ID NO 43
<211> LENGTH: 6
<212> TYPE: PRT
<213> ORGANISM: artificial sequence
<220> FEATURE:
<223> OTHER INFORMATION: CDR3

<400> SEQUENCE: 43

```
Arg Trp Ala Glu Gly Tyr
1               5
```

<210> SEQ ID NO 44
<211> LENGTH: 30
<212> TYPE: PRT
<213> ORGANISM: artificial sequence
<220> FEATURE:

```
<223> OTHER INFORMATION: FR1

<400> SEQUENCE: 44

Asp Val Gln Leu Gln Glu Ser Gly Gly Gly Leu Val Gln Pro Gly Gly
1               5                   10                  15

Ser Leu Arg Leu Ser Cys Ala Ala Ser Gly Phe Leu Phe Ser
            20                  25                  30

<210> SEQ ID NO 45
<211> LENGTH: 32
<212> TYPE: PRT
<213> ORGANISM: artificial sequence
<220> FEATURE:
<223> OTHER INFORMATION: FR3

<400> SEQUENCE: 45

Arg Phe Thr Ile Ser Arg Asp Asn Ala Lys Asn Thr Leu Thr Leu Gln
1               5                   10                  15

Leu Asn Ser Leu Lys Thr Glu Asp Thr Ala Met Tyr Tyr Cys Ala Lys
            20                  25                  30

<210> SEQ ID NO 46
<211> LENGTH: 5
<212> TYPE: PRT
<213> ORGANISM: artificial sequence
<220> FEATURE:
<223> OTHER INFORMATION: CDR1

<400> SEQUENCE: 46

Arg Tyr Ser Met Ser
1               5

<210> SEQ ID NO 47
<211> LENGTH: 17
<212> TYPE: PRT
<213> ORGANISM: artificial sequence
<220> FEATURE:
<223> OTHER INFORMATION: CDR2

<400> SEQUENCE: 47

Gly Ile Thr Asn Gly Gly Ser Ile Thr Lys Tyr Ala Asp Ser Val Lys
1               5                   10                  15

Gly

<210> SEQ ID NO 48
<211> LENGTH: 15
<212> TYPE: PRT
<213> ORGANISM: artificial sequence
<220> FEATURE:
<223> OTHER INFORMATION: CDR3

<400> SEQUENCE: 48

Gly Ala Gly Glu Tyr Gly Pro Val Ser Asp Tyr Val Phe Ser Leu
1               5                   10                  15

<210> SEQ ID NO 49
<211> LENGTH: 30
<212> TYPE: PRT
<213> ORGANISM: artificial sequence
<220> FEATURE:
<223> OTHER INFORMATION: FR1

<400> SEQUENCE: 49

Asp Val Gln Leu Gln Glu Ser Gly Gly Gly Ser Val Gln Ala Gly Gly
1               5                   10                  15
```

Ser Leu Arg Leu Ser Cys Ala Ala Ser Gly Tyr Thr Ile Gly
            20                  25                  30

<210> SEQ ID NO 50
<211> LENGTH: 32
<212> TYPE: PRT
<213> ORGANISM: artificial sequence
<220> FEATURE:
<223> OTHER INFORMATION: FR3

<400> SEQUENCE: 50

Arg Phe Ala Ile Ser Glu Asp Asn Ala Lys Asn Thr Val Tyr Leu His
1               5                   10                  15

Met Asn Leu Leu Lys Pro Glu Asp Thr Ala Met Tyr Tyr Cys Ala Ala
            20                  25                  30

<210> SEQ ID NO 51
<211> LENGTH: 5
<212> TYPE: PRT
<213> ORGANISM: artificial sequence
<220> FEATURE:
<223> OTHER INFORMATION: CDR1

<400> SEQUENCE: 51

Ser Asn Tyr Met Gly
1               5

<210> SEQ ID NO 52
<211> LENGTH: 17
<212> TYPE: PRT
<213> ORGANISM: artificial sequence
<220> FEATURE:
<223> OTHER INFORMATION: CDR2

<400> SEQUENCE: 52

Ala Ile Tyr Thr Gly Gly Gly Asn Thr Tyr Tyr Ala Asp Ser Val Lys
1               5                   10                  15

Gly

<210> SEQ ID NO 53
<211> LENGTH: 16
<212> TYPE: PRT
<213> ORGANISM: artificial sequence
<220> FEATURE:
<223> OTHER INFORMATION: CDR3

<400> SEQUENCE: 53

Asp Leu Arg Leu Arg Val Ala Val Leu His Pro Tyr Gly Tyr Asn Tyr
1               5                   10                  15

<210> SEQ ID NO 54
<211> LENGTH: 30
<212> TYPE: PRT
<213> ORGANISM: artificial sequence
<220> FEATURE:
<223> OTHER INFORMATION: FR1

<400> SEQUENCE: 54

Asp Val Gln Leu Gln Glu Ser Gly Gly Gly Leu Val Gln Pro Gly Gly
1               5                   10                  15

Ser Leu Arg Leu Ser Cys Ala Val Ser Gly Phe Thr Phe Ser
            20                  25                  30

<210> SEQ ID NO 55

```
<211> LENGTH: 15
<212> TYPE: PRT
<213> ORGANISM: artificial sequence
<220> FEATURE:
<223> OTHER INFORMATION: FR2

<400> SEQUENCE: 55

Ser Trp Val Arg Gln Ala Pro Gly Lys Gly Leu Glu Trp Val Ser
1               5                   10                  15

<210> SEQ ID NO 56
<211> LENGTH: 32
<212> TYPE: PRT
<213> ORGANISM: artificial sequence
<220> FEATURE:
<223> OTHER INFORMATION: FR3

<400> SEQUENCE: 56

Arg Phe Thr Ile Ser Arg Asp Asn Ala Lys Asn Thr Leu Tyr Leu Gln
1               5                   10                  15

Leu Asn Asn Leu Lys Thr Glu Asp Thr Ala Met Tyr Tyr Cys Thr Lys
            20                  25                  30

<210> SEQ ID NO 57
<211> LENGTH: 11
<212> TYPE: PRT
<213> ORGANISM: artificial sequence
<220> FEATURE:
<223> OTHER INFORMATION: FR4

<400> SEQUENCE: 57

Gly Gly Gln Gly Thr Gln Val Thr Val Ser Ser
1               5                   10

<210> SEQ ID NO 58
<211> LENGTH: 4
<212> TYPE: PRT
<213> ORGANISM: artificial sequence
<220> FEATURE:
<223> OTHER INFORMATION: CDR1

<400> SEQUENCE: 58

Asn Tyr Ala Met
1

<210> SEQ ID NO 59
<211> LENGTH: 16
<212> TYPE: PRT
<213> ORGANISM: artificial sequence
<220> FEATURE:
<223> OTHER INFORMATION: CDR2

<400> SEQUENCE: 59

Arg Ile Ser Ser Ser Gly Ile Thr Tyr Tyr Ala Asp Ser Val Lys Gly
1               5                   10                  15

<210> SEQ ID NO 60
<211> LENGTH: 5
<212> TYPE: PRT
<213> ORGANISM: artificial sequence
<220> FEATURE:
<223> OTHER INFORMATION: CDR3

<400> SEQUENCE: 60

Ser Ser Glu Ala Pro
1               5
```

```
<210> SEQ ID NO 61
<211> LENGTH: 30
<212> TYPE: PRT
<213> ORGANISM: artificial sequence
<220> FEATURE:
<223> OTHER INFORMATION: FR1

<400> SEQUENCE: 61

Asp Val Gln Leu Gln Glu Ser Gly Gly Gly Ser Val Gln Ala Gly Gly
1               5                   10                  15

Ser Leu Arg Leu Ser Cys Ala Ala Ser Gly Ala Ile Tyr Arg
            20                  25                  30

<210> SEQ ID NO 62
<211> LENGTH: 32
<212> TYPE: PRT
<213> ORGANISM: artificial sequence
<220> FEATURE:
<223> OTHER INFORMATION: FR3

<400> SEQUENCE: 62

Arg Phe Thr Ile Ser Gln Asp Asn Ala Lys Asn Thr Val Tyr Leu Gln
1               5                   10                  15

Met Asn Asp Leu Lys Pro Glu Asp Thr Ala Met Tyr Tyr Cys Ala Ala
            20                  25                  30

<210> SEQ ID NO 63
<211> LENGTH: 5
<212> TYPE: PRT
<213> ORGANISM: artificial sequence
<220> FEATURE:
<223> OTHER INFORMATION: CDR1

<400> SEQUENCE: 63

Gly Asn Tyr Met Gly
1               5

<210> SEQ ID NO 64
<211> LENGTH: 17
<212> TYPE: PRT
<213> ORGANISM: artificial sequence
<220> FEATURE:
<223> OTHER INFORMATION: CDR2

<400> SEQUENCE: 64

Ala Ile Ala Thr Asn Gly Arg Thr Thr Tyr Tyr Ala Asp Ser Val Lys
1               5                   10                  15

Gly

<210> SEQ ID NO 65
<211> LENGTH: 19
<212> TYPE: PRT
<213> ORGANISM: artificial sequence
<220> FEATURE:
<223> OTHER INFORMATION: CDR3

<400> SEQUENCE: 65

Asp Asn Ser Trp Ser Cys Thr Val Val Gly Gly Leu Leu Ala Pro Ala
1               5                   10                  15

Tyr Asn Tyr

<210> SEQ ID NO 66
<211> LENGTH: 30
<212> TYPE: PRT
```

```
<213> ORGANISM: artificial sequence
<220> FEATURE:
<223> OTHER INFORMATION: FR1

<400> SEQUENCE: 66

Asp Val Gln Leu Gln Glu Ser Gly Gly Gly Ser Val Gln Ala Gly Gly
1               5                   10                  15

Ser Leu Arg Leu Ser Cys Ala Ala Ser Arg Phe Thr Tyr Ser
            20                  25                  30

<210> SEQ ID NO 67
<211> LENGTH: 32
<212> TYPE: PRT
<213> ORGANISM: artificial sequence
<220> FEATURE:
<223> OTHER INFORMATION: FR3

<400> SEQUENCE: 67

Arg Phe Thr Ile Ser Leu Asp Ile Ala Lys Lys Thr Leu Ser Leu Gln
1               5                   10                  15

Met Asp Ser Leu Lys Ser Glu Asp Thr Ala Met Tyr Tyr Cys Ala Ala
            20                  25                  30

<210> SEQ ID NO 68
<211> LENGTH: 5
<212> TYPE: PRT
<213> ORGANISM: artificial sequence
<220> FEATURE:
<223> OTHER INFORMATION: CDR1

<400> SEQUENCE: 68

Trp Tyr Cys Met Gly
1               5

<210> SEQ ID NO 69
<211> LENGTH: 17
<212> TYPE: PRT
<213> ORGANISM: artificial sequence
<220> FEATURE:
<223> OTHER INFORMATION: CDR2

<400> SEQUENCE: 69

Ala Ile Cys Thr Thr Pro Ser Arg Thr Tyr Ala Ala Asp Ser Val Lys
1               5                   10                  15

Gly

<210> SEQ ID NO 70
<211> LENGTH: 18
<212> TYPE: PRT
<213> ORGANISM: artificial sequence
<220> FEATURE:
<223> OTHER INFORMATION: CDR3

<400> SEQUENCE: 70

Asp Thr Arg Gly Ala Ile Gly Phe Phe Lys Gly Ser Gly Pro Ala Ile
1               5                   10                  15

Pro Tyr

<210> SEQ ID NO 71
<211> LENGTH: 123
<212> TYPE: PRT
<213> ORGANISM: artificial sequence
<220> FEATURE:
<223> OTHER INFORMATION: 1# nanobody
```

```
<400> SEQUENCE: 71

Asp Val Gln Leu Gln Glu Ser Gly Gly Gly Ser Val Gln Ala Gly Gly
1               5                   10                  15

Ser Leu Arg Leu Ser Cys Ala Ala Ser Gly Val Ala His Arg Arg Tyr
            20                  25                  30

Tyr Met Ser Trp Phe Arg Gln Ala Pro Gly Lys Glu Arg Glu Gly Val
        35                  40                  45

Ala Ser Ile Tyr Ile Gly Ser Gly Ser Thr Asp Tyr Val Asp Ser Val
    50                  55                  60

Lys Gly Arg Phe Thr Ile Ser Gln Asp Asn Ala Asn Asp Met Val Tyr
65                  70                  75                  80

Leu Gln Met Leu Ser Leu Lys Pro Glu Asp Thr Ala Met Tyr Tyr Cys
                85                  90                  95

Ala Ala Gly Leu Tyr Gly Gly Arg Trp Asp Arg Ala Gly Tyr Lys Tyr
            100                 105                 110

Trp Gly Gln Gly Thr Gln Val Thr Val Ser Ser
        115                 120

<210> SEQ ID NO 72
<211> LENGTH: 131
<212> TYPE: PRT
<213> ORGANISM: artificial sequence
<220> FEATURE:
<223> OTHER INFORMATION: 2# nanobody

<400> SEQUENCE: 72

Asp Val Gln Leu Gln Glu Ser Gly Gly Gly Ser Val Gln Ala Gly Gly
1               5                   10                  15

Ser Leu Arg Leu Ser Cys Thr Ala Ser Gly Tyr Thr Arg Ser Thr Ile
            20                  25                  30

Trp Ile Gly Trp Phe Arg Gln Ala Pro Gly Lys Glu Arg Glu Gly Val
        35                  40                  45

Ala Ala Ile Tyr Ile Gly Ser Gly Ala Thr Tyr Tyr Val Asp Ser Val
    50                  55                  60

Lys Gly Arg Phe Thr Ile Ser Gln Asp Asn Ala Lys Asn Ala Lys Asn
65                  70                  75                  80

Thr Val Tyr Leu Gln Met Asn Ser Leu Lys Pro Glu Asp Thr Ala Met
                85                  90                  95

Tyr Tyr Cys Ala Ala Thr Gly Gly Thr Val Gly Ser Met Val Arg Phe
            100                 105                 110

Ser Pro Val Gly Asp Phe Gly Tyr Trp Gly Gln Gly Thr Gln Val Thr
            115                 120                 125

Val Ser Ser
    130

<210> SEQ ID NO 73
<211> LENGTH: 123
<212> TYPE: PRT
<213> ORGANISM: artificial sequence
<220> FEATURE:
<223> OTHER INFORMATION: 3# nanobody

<400> SEQUENCE: 73

Asp Val Gln Leu Gln Glu Ser Gly Gly Gly Leu Val Gln Pro Gly Gly
1               5                   10                  15

Ser Leu Arg Leu Ser Cys Ala Ala Ser Gly Phe Thr Phe Thr Asn Tyr
            20                  25                  30
```

```
Ala Met Ser Trp Val Arg Gln Ala Pro Gly Lys Gly Leu Glu Trp Val
            35                  40                  45

Ser Gly Ile Asn Ser Asp Gly Gly Thr Tyr Tyr Ser Asn Ser Val Lys
 50                      55                  60

Gly Arg Ser Thr Ile Ser Arg Asp Asn Ala Lys Asn Thr Leu Tyr Leu
 65                  70                  75                  80

Gln Leu Asn Ser Leu Glu Thr Glu Asp Thr Ala Met Tyr Tyr Cys Ala
                 85                  90                  95

Lys Gly Asn Gly Pro Ser Trp Thr Leu Gly Ser Val Asp Val Asn Ser
                100                 105                 110

Arg Gly Gln Gly Thr Gln Val Thr Val Ser Ser
            115                 120

<210> SEQ ID NO 74
<211> LENGTH: 126
<212> TYPE: PRT
<213> ORGANISM: artificial sequence
<220> FEATURE:
<223> OTHER INFORMATION: 4# nanobody

<400> SEQUENCE: 74

Asp Val Gln Leu Gln Glu Ser Gly Gly Gly Ser Val Gln Ala Gly Gly
 1               5                  10                  15

Ser Leu Arg Leu Ser Cys Ala Ala Ser Gly Asp Thr Tyr Arg Arg Asn
            20                  25                  30

Thr Met Gly Trp Phe Arg Gln Ala Pro Gly Lys Glu Arg Glu Gly Val
            35                  40                  45

Ala Ala Ile Tyr Thr Gly Gly Thr Ser Thr Ala Tyr Ala Asp Ser Val
 50                      55                  60

Arg Gly Arg Phe Thr Ile Ser Gln Asp Ser Ala Lys Asn Thr Val Tyr
 65                  70                  75                  80

Leu Gln Met Asn Ser Leu Lys Pro Glu Asp Thr Ala Ile Tyr Tyr Cys
                 85                  90                  95

Ala Ala Gly Ser Val Trp Ser Arg Tyr Thr Trp Ser Trp Pro Ser Thr
                100                 105                 110

Tyr Ser Tyr Trp Gly Gln Gly Thr Gln Val Thr Val Ser Ser
            115                 120                 125

<210> SEQ ID NO 75
<211> LENGTH: 124
<212> TYPE: PRT
<213> ORGANISM: artificial sequence
<220> FEATURE:
<223> OTHER INFORMATION: 5# nanobody

<400> SEQUENCE: 75

Asp Val Gln Leu Gln Glu Ser Gly Gly Gly Ser Val Gln Ala Gly Gly
 1               5                  10                  15

Ser Leu Arg Leu Ser Cys Ala Ser Glu Tyr Ser Tyr Ser Arg Lys
            20                  25                  30

Trp Met Gly Trp Phe Arg Gln Ala Pro Gly Lys Glu Arg Glu Gly Val
            35                  40                  45

Ala Ala Ile Tyr Thr Ser Gly Arg Thr Ala Val Ala Asp Ser Val Lys
 50                      55                  60

Gly Arg Phe Thr Ile Ser Gln Asp Ile Ala Glu Asn Thr Val Tyr Leu
 65                  70                  75                  80

Arg Met Asn Ser Leu Lys Pro Glu Asp Thr Ala Met Tyr Tyr Cys Ala
                 85                  90                  95
```

```
Ala Leu Thr Gly Ala Ser Asp Ser Pro Leu Arg Pro Ser Glu Tyr Asn
            100                 105                 110

Tyr Trp Gly Gln Gly Thr Gln Val Thr Val Ser Ser
        115                 120
```

<210> SEQ ID NO 76
<211> LENGTH: 130
<212> TYPE: PRT
<213> ORGANISM: artificial sequence
<220> FEATURE:
<223> OTHER INFORMATION: 6# nanobody

<400> SEQUENCE: 76

```
Asp Val Gln Leu Gln Glu Ser Gly Gly Gly Ser Val Gln Ala Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Gly Leu Glu Trp Val
        35                  40                  45

Ser Ala Ile Asn Ser Gly Gly Gly Ser Thr Tyr Tyr Ala Asp Ser Val
    50                  55                  60

Lys Gly Arg Phe Thr Ile Ser Arg Asp Asn Ala Lys Asn Thr Met Tyr
65                  70                  75                  80

Leu Gln Met Asn Ser Leu Lys Pro Glu Asp Thr Ala Met Tyr Tyr Cys
                85                  90                  95

Ala Ala Asp Pro Gly Ser Ser Leu Ala Val Gly Ala Trp Leu Lys Ala
            100                 105                 110

Ala Asp Pro Phe Tyr Gly Tyr Trp Gly Gln Gly Thr Gln Val Thr Val
        115                 120                 125

Ser Ser
    130
```

<210> SEQ ID NO 77
<211> LENGTH: 131
<212> TYPE: PRT
<213> ORGANISM: artificial sequence
<220> FEATURE:
<223> OTHER INFORMATION: 7# nanobody

<400> SEQUENCE: 77

```
Asp Val Gln Leu Gln Glu Ser Gly Gly Gly Ser Val Gln Ala Gly Gly
1               5                   10                  15

Ser Leu Arg Leu Ser Cys Thr Ala Ser Gly Tyr Thr Arg Ser Thr Ile
            20                  25                  30

Trp Ile Gly Trp Phe Arg Gln Ala Pro Gly Lys Glu Arg Glu Gly Val
        35                  40                  45

Ala Ala Ile Tyr Ile Gly Ser Gly Ala Thr Tyr Tyr Val Asp Ser Val
    50                  55                  60

Lys Gly Arg Phe Thr Ile Ser Gln Asp Asn Ala Lys Asn Ala Lys Asn
65                  70                  75                  80

Thr Val Tyr Leu Gln Met Asn Ser Leu Lys Pro Glu Asp Thr Ala Met
                85                  90                  95

Tyr Tyr Cys Ala Ala Thr Ser Gly Thr Val Gly Ser Met Val Arg Phe
            100                 105                 110

Ser Pro Val Gly Asp Phe Gly Tyr Trp Gly Gln Gly Thr Gln Val Thr
        115                 120                 125

Val Ser Ser
```

-continued

130

<210> SEQ ID NO 78
<211> LENGTH: 115
<212> TYPE: PRT
<213> ORGANISM: artificial sequence
<220> FEATURE:
<223> OTHER INFORMATION: 8# nanobody

<400> SEQUENCE: 78

Asp Val Gln Leu Gln Glu Ser Gly Gly Gly Leu Val Gln Pro Gly Gly
1               5                   10                  15

Ser Leu Arg Leu Ser Cys Ala Ala Ser Gly Phe Thr Phe Ser Gly Val
            20                  25                  30

Asp Met Ser Trp Val Arg Gln Ala Pro Gly Arg Gly Leu Glu Trp Val
        35                  40                  45

Ser Gly Phe Gly Ser Gly Gly Glu Ser Pro Ser Tyr Ala Asp Ser Val
    50                  55                  60

Lys Gly Arg Phe Thr Ile Ser Arg Asp Asn Ala Lys Lys Met Leu Tyr
65                  70                  75                  80

Leu Gln Met Asp Ser Leu Lys Pro Glu Asp Thr Ala Val Tyr Tyr Cys
                85                  90                  95

Ala Thr Arg Trp Ala Glu Gly Tyr Trp Gly Gln Gly Thr Gln Val Thr
            100                 105                 110

Val Ser Ser
        115

<210> SEQ ID NO 79
<211> LENGTH: 124
<212> TYPE: PRT
<213> ORGANISM: artificial sequence
<220> FEATURE:
<223> OTHER INFORMATION: 9# nanobody

<400> SEQUENCE: 79

Asp Val Gln Leu Gln Glu Ser Gly Gly Gly Leu Val Gln Pro Gly Gly
1               5                   10                  15

Ser Leu Arg Leu Ser Cys Ala Ala Ser Gly Phe Leu Phe Ser Arg Tyr
            20                  25                  30

Ser Met Ser Trp Val Arg Gln Ala Pro Gly Lys Gly Leu Glu Trp Val
        35                  40                  45

Ser Gly Ile Thr Asn Gly Gly Ser Ile Thr Lys Tyr Ala Asp Ser Val
    50                  55                  60

Lys Gly Arg Phe Thr Ile Ser Arg Asp Asn Ala Lys Asn Thr Leu Thr
65                  70                  75                  80

Leu Gln Leu Asn Ser Leu Lys Thr Glu Asp Thr Ala Met Tyr Tyr Cys
                85                  90                  95

Ala Lys Gly Ala Gly Glu Tyr Gly Pro Val Ser Asp Tyr Val Phe Ser
            100                 105                 110

Leu Arg Gly Gln Gly Thr Gln Val Thr Val Ser Ser
        115                 120

<210> SEQ ID NO 80
<211> LENGTH: 125
<212> TYPE: PRT
<213> ORGANISM: artificial sequence
<220> FEATURE:
<223> OTHER INFORMATION: 10# nanobody

<400> SEQUENCE: 80

```
Asp Val Gln Leu Gln Glu Ser Gly Gly Gly Ser Val Gln Ala Gly Gly
1               5                   10                  15

Ser Leu Arg Leu Ser Cys Ala Ala Ser Gly Tyr Thr Ile Gly Ser Asn
            20                  25                  30

Tyr Met Gly Trp Phe Arg Gln Ala Pro Gly Lys Glu Arg Glu Gly Val
        35                  40                  45

Ala Ala Ile Tyr Thr Gly Gly Asn Thr Tyr Ala Asp Ser Val
    50                  55                  60

Lys Gly Arg Phe Ala Ile Ser Glu Asp Asn Ala Lys Asn Thr Val Tyr
65                  70                  75                  80

Leu His Met Asn Leu Lys Pro Glu Asp Thr Ala Met Tyr Tyr Cys
                85                  90                  95

Ala Ala Asp Leu Arg Leu Arg Val Ala Val Leu His Pro Tyr Gly Tyr
            100                 105                 110

Asn Tyr Trp Gly Gln Gly Thr Gln Val Thr Val Ser Ser
        115                 120                 125
```

<210> SEQ ID NO 81
<211> LENGTH: 113
<212> TYPE: PRT
<213> ORGANISM: artificial sequence
<220> FEATURE:
<223> OTHER INFORMATION: 11# nanobody

<400> SEQUENCE: 81

```
Asp Val Gln Leu Gln Glu Ser Gly Gly Gly Leu Val Gln Pro Gly Gly
1               5                   10                  15

Ser Leu Arg Leu Ser Cys Ala Val Ser Gly Phe Thr Phe Ser Asn Tyr
            20                  25                  30

Ala Met Ser Trp Val Arg Gln Ala Pro Gly Lys Gly Leu Glu Trp Val
        35                  40                  45

Ser Arg Ile Ser Ser Ser Gly Ile Thr Tyr Tyr Ala Asp Ser Val Lys
    50                  55                  60

Gly Arg Phe Thr Ile Ser Arg Asp Asn Ala Lys Asn Thr Leu Tyr Leu
65                  70                  75                  80

Gln Leu Asn Asn Leu Lys Thr Glu Asp Thr Ala Met Tyr Tyr Cys Thr
                85                  90                  95

Lys Ser Ser Glu Ala Pro Gly Gly Gln Gly Thr Gln Val Thr Val Ser
            100                 105                 110

Ser
```

<210> SEQ ID NO 82
<211> LENGTH: 128
<212> TYPE: PRT
<213> ORGANISM: artificial sequence
<220> FEATURE:
<223> OTHER INFORMATION: 12# nanobody

<400> SEQUENCE: 82

```
Asp Val Gln Leu Gln Glu Ser Gly Gly Gly Ser Val Gln Ala Gly Gly
1               5                   10                  15

Ser Leu Arg Leu Ser Cys Ala Ala Ser Gly Ala Ile Tyr Arg Gly Asn
            20                  25                  30

Tyr Met Gly Trp Phe Arg Gln Ala Pro Gly Lys Glu Arg Glu Gly Val
        35                  40                  45

Ala Ala Ile Ala Thr Asn Gly Arg Thr Thr Tyr Tyr Ala Asp Ser Val
    50                  55                  60
```

Lys Gly Arg Phe Thr Ile Ser Gln Asp Asn Ala Lys Asn Thr Val Tyr
65                  70                  75                  80

Leu Gln Met Asn Asp Leu Lys Pro Glu Asp Thr Ala Met Tyr Tyr Cys
                85                  90                  95

Ala Ala Asp Asn Ser Trp Ser Cys Thr Val Val Gly Gly Leu Leu Ala
            100                 105                 110

Pro Ala Tyr Asn Tyr Trp Gly Gln Gly Thr Gln Val Thr Val Ser Ser
        115                 120                 125

<210> SEQ ID NO 83
<211> LENGTH: 127
<212> TYPE: PRT
<213> ORGANISM: artificial sequence
<220> FEATURE:
<223> OTHER INFORMATION: 13# nanobody

<400> SEQUENCE: 83

Asp Val Gln Leu Gln Glu Ser Gly Gly Ser Val Gln Ala Gly Gly
1               5                   10                  15

Ser Leu Arg Leu Ser Cys Ala Ala Ser Arg Phe Thr Tyr Ser Trp Tyr
            20                  25                  30

Cys Met Gly Trp Phe Arg Gln Ala Pro Gly Lys Glu Arg Glu Gly Val
            35                  40                  45

Ala Ala Ile Cys Thr Thr Pro Ser Arg Thr Tyr Ala Ala Asp Ser Val
        50                  55                  60

Lys Gly Arg Phe Thr Ile Ser Leu Asp Ile Ala Lys Lys Thr Leu Ser
65                  70                  75                  80

Leu Gln Met Asp Ser Leu Lys Ser Glu Asp Thr Ala Met Tyr Tyr Cys
                85                  90                  95

Ala Ala Asp Thr Arg Gly Ala Ile Gly Phe Phe Lys Gly Ser Gly Pro
            100                 105                 110

Ala Ile Pro Tyr Trp Gly Gln Gly Thr Gln Val Thr Val Ser Ser
        115                 120                 125

<210> SEQ ID NO 84
<211> LENGTH: 369
<212> TYPE: DNA
<213> ORGANISM: artificial sequence
<220> FEATURE:
<223> OTHER INFORMATION: DNA of 1# nanobody

<400> SEQUENCE: 84
gatgtgcagc tgcaggagtc tggaggaggc tcggtgcagg ctggagggtc tctgagactc      60
tcctgtgcag cctctggtgt cgcccacagg cgctactaca tgtcctggtt ccgccaggct     120
ccagggaagg agcgcgaggg ggtcgcatcc atttatattg gtagtggtag cacagactat     180
gtcgactccg tgaagggccg attcaccatc tcccaagaca cgccaacga catggtgtat     240 ctgcaaatgc tcagcctcaa acctgaggac actgccatgt actactgtgc ggcaggcctt     300
tacggtggta gatgggatcg ggcccagtat aagtactggg gccaggggac ccaggtcacc     360
gtctcctca                                                            369

<210> SEQ ID NO 85
<211> LENGTH: 393
<212> TYPE: DNA
<213> ORGANISM: artificial sequence
<220> FEATURE:
<223> OTHER INFORMATION: DNA of 2# nanobody

<400> SEQUENCE: 85

```
gatgtgcagc tgcaggagtc tggaggaggc tcggtgcagg ctggagggtc tctgagactc    60
tcctgtacag cctccggata cacccgcagt accatttgga taggctggtt ccgccaggct   120
ccagggaagg agcgcgaggg ggtcgcagct atttatattg gtagtggcgc gacatactat   180
gtggactccg tgaagggccg attcaccatc tcccaagaca cgccaagaac cgccaagaac   240
acggtgtatc tgcagatgaa cagcctgaaa cctgaggaca ctgccatgta ctactgtgcg   300
gcaacgggcg gtactgtagg aagtatggtc cgattctccc cagtgggcga ctttggttat   360
tggggccagg ggacccaggt caccgtctcc tca                                393
```

<210> SEQ ID NO 86
<211> LENGTH: 369
<212> TYPE: DNA
<213> ORGANISM: artificial sequence
<220> FEATURE:
<223> OTHER INFORMATION: DNA of 3# nanobody

<400> SEQUENCE: 86

```
gatgtgcagc tgcaggagtc tggaggaggc ttggtgcagc tggggggtc tctgagactc     60
tcctgtgcag cctctggatt caccttcaca aactatgcca tgagctgggt ccgccaggct   120
ccagggaagg gactcgagtg ggtctcaggt attaatagtg atggtggcac atactattca   180
aactccgtga agggccgaag caccatctcc agagacaacg ccaagaacac gctgtatctg   240
caattgaaca gcctggagac tgaggacacg gccatgtatt actgtgcaaa aggaaacggc   300
ccgtcttgga ccctggggag cgtggacgtt aactcccggg ccaggggac ccaggtcacc   360
gtctcctca                                                           369
```

<210> SEQ ID NO 87
<211> LENGTH: 378
<212> TYPE: DNA
<213> ORGANISM: artificial sequence
<220> FEATURE:
<223> OTHER INFORMATION: DNA of 4# nanobody

<400> SEQUENCE: 87

```
gatgtgcagc tgcaggagtc tggaggaggc tcggtgcagg ctggagggtc tctgagactc    60
tcctgtgcag cctctggaga cacttacagg cgcaacacca tggctgtt ccgccaggct    120
ccggggaagg agcgcgaggg ggtcgcagct atttatactg gtggtactag tacagcctat   180
gccgactccg tgaggggccg attcaccatc tcccaagaca cgccaagaa cacgtgtat    240
ctgcaaatga acagcctgaa acctgaggac actgccatat actactgtgc ggcaggctca   300
gtgtggtccc gttatacatg gtcctggccc agtacgtata gctactgggg ccaggggacc   360
caggtcaccg tctcctca                                                 378
```

<210> SEQ ID NO 88
<211> LENGTH: 372
<212> TYPE: DNA
<213> ORGANISM: artificial sequence
<220> FEATURE:
<223> OTHER INFORMATION: DNA of 5# nanobody

<400> SEQUENCE: 88

```
gatgtgcagc tgcaggagtc tggaggaggc tcggtgcagg ctggagggtc tctgagactc    60
tcctgtgcag cctctgaata cagctacagt aggaagtgga tgggctggtt ccgccaggct   120
ccagggaagg agcgcgaggg ggtcgcagct atttatacta gtggtaggac agccgttgcc   180
```

```
gactccgtga agggccgatt caccatctcc caagacatcg ccgagaacac ggtgtatctg    240
cgtatgaaca gcctgaaacc tgaggacact gccatgtact actgtgcggc actcacaggt    300
gctagcgact caccgctacg cccaagcgag tataactact ggggccaggg gacccaggtc    360
accgtctcct ca                                                        372

<210> SEQ ID NO 89
<211> LENGTH: 390
<212> TYPE: DNA
<213> ORGANISM: artificial sequence
<220> FEATURE:
<223> OTHER INFORMATION: DNA of 6# nanobody

<400> SEQUENCE: 89
gatgtgcagc tgcaggagtc tggaggaggc tcggtgcagg ctggagggtc tctgagactc     60
tcctgtgcag cctctggatt cacattcagt agctacgaca tgagctgggt ccgccaggct    120
ccagggaagg ggctcgagtg ggtctcagct attaatagtg gtggtggtag cacatactat    180
gcagactccg tgaagggccg attcaccatc tccagagaca cgccaagaa cacgatgtat     240 ctgcaaatga acagcctgaa acctgaggac actgccatgt actactgtgc ggcagatcct    300
ggttcaagtt tggcggtggg agcttggttg aaggcggcgg atcccttcta tggttactgg    360
ggccagggga cccaggtcac cgtctcctca                                     390

<210> SEQ ID NO 90
<211> LENGTH: 393
<212> TYPE: DNA
<213> ORGANISM: artificial sequence
<220> FEATURE:
<223> OTHER INFORMATION: DNA of 7# nanobody

<400> SEQUENCE: 90
gatgtgcagc tgcaggagtc tggaggaggc tcggtgcagg ctggagggtc tctgagactc     60
tcctgtacag cctccggata caccgcagt accatttgga taggctggtt ccgccaggct     120
ccagggaagg agcgcgaggg ggtcgcagct atttatattg gtagtggcgc gacatactat    180
gtggactccg tgaagggccg attcaccatc tcccaagaca cgccaagaa cgccaagaac     240 acggtgtatc tgcagatgaa cagcctgaaa cctgaggaca ctgccatgta ctactgtgcg    300
gcaacgagcg gtactgtagg aagtatggtc cgattctccc cagtgggcga ctttggttat    360
tggggccagg ggacccaggt caccgtctcc tca                                 393

<210> SEQ ID NO 91
<211> LENGTH: 345
<212> TYPE: DNA
<213> ORGANISM: artificial sequence
<220> FEATURE:
<223> OTHER INFORMATION: DNA of 8# nanobody

<400> SEQUENCE: 91
gatgtgcagc tgcaggagtc tggaggaggc ttggtgcagc tggggggtc tctgagactc      60 tcctgtgcag cctctggatt cacattcagt ggcgtcgaca tgagctgggt ccgccaggct    120
ccagggaggg ggctcgagtg ggtctcaggg tttggtagtg gtggtgaaag ccatcatat     180 gcagactccg tgaagggccg attcaccatc tccagagaca cgccaagaa aatgctgtat     240 ctgcagatgg acagtttgaa acctgaggac acagccgtgt attactgcgc cacccgctgg    300
gctgagggct actggggcca ggggacccag gtcaccgtct cctca                    345
```

<210> SEQ ID NO 92
<211> LENGTH: 372
<212> TYPE: DNA
<213> ORGANISM: artificial sequence
<220> FEATURE:
<223> OTHER INFORMATION: DNA of 9# nanobody

<400> SEQUENCE: 92

```
gatgtgcagc tgcaggagtc tggaggaggc ttggtgcagc ctgggggtc tctgagactc      60 tcctgtgcag cctctggatt cctcttcagt agatattcca tgagttgggt ccgccaggct    120
ccagggaagg gactcgagtg gtctcaggt attacgaatg gtggtagcat tacaaagtat      180
gcagactccg tgaagggccg attcaccatc tccagagaca acgccaagaa cacactgact    240
ctgcaactga acagcctgaa aactgaggac acggccatgt attactgtgc caaaggcgcg    300
ggggagtatg ccctgttag tgactatgtc ttctctctca ggggccaggg gacccaggtc     360
accgtctcct ca                                                         372
```

<210> SEQ ID NO 93
<211> LENGTH: 375
<212> TYPE: DNA
<213> ORGANISM: artificial sequence
<220> FEATURE:
<223> OTHER INFORMATION: DNA of 10# nanobody

<400> SEQUENCE: 93

```
gatgtgcagc tgcaggagtc tggaggaggc tcggtgcagg ctggagggtc tctgagactc    60
tcctgtgcag cctctggata caccatcggt agcaactaca tgggctggtt ccgccaggct    120
ccagggaagg agcgcgaggg ggtcgcagct atttatactg tggtggtaa tacatactat    180 gccgactccg tgaagggccg attcgccatc tccgaagaca acgccaagaa cacggtgtat    240
ctgcacatga acctcctgaa acctgaggac actgccatgt actactgtgc ggcagacttg    300
agactacggg ttgctgtact ccacccgtat gggtataact actggggcca ggggacccag    360
gtcaccgtct cctca                                                      375
```

<210> SEQ ID NO 94
<211> LENGTH: 339
<212> TYPE: DNA
<213> ORGANISM: artificial sequence
<220> FEATURE:
<223> OTHER INFORMATION: DNA of 11# nanobody

<400> SEQUENCE: 94

```
gatgtgcagc tgcaggagtc tggaggaggc ttggtgcagc ctgggggtc tctgagactc      60 tcctgtgcag tctctggatt caccttcagt aactatgcca tgagctgggt ccgccaggct    120
ccagggaagg ggctcgagtg gtctcacgt attagtagta gtggtattac atactatgca    180
gactccgtga agggccgatt caccatctcc agagacaacg ccaagaacac gctgtatcta    240
caattgaaca acctgaaaac tgaggacacg gccatgtatt actgtacaaa aagttccgag    300
gccccgggtg ccaggggac ccaggtcacc gtctcctca                             339
```

<210> SEQ ID NO 95
<211> LENGTH: 384
<212> TYPE: DNA
<213> ORGANISM: artificial sequence
<220> FEATURE:
<223> OTHER INFORMATION: DNA of 12# nanobody

<400> SEQUENCE: 95

```
gatgtgcagc tgcaggagtc tggaggaggc tcggtacagg ctggagggtc tctgagactc      60
tcctgtgcag cctctggagc catctacaga ggcaactaca tgggctggtt ccgccaggct     120
ccagggaagg agcgcgaggg ggtcgcggct atcgctacta atggtcgtac aacatactat     180
gccgactccg tgaagggccg attcaccatc tcccaagaca acgccaagaa cacggtgtat     240
ctgcaaatga acgacctgaa acctgaggac actgccatgt actactgtgc ggcagacaac     300
tcttggtcct gtacggtggt aggtgggcta ctggcgcctg cctataacta ctggggccag     360
gggacccagg tcaccgtctc ctca                                            384

<210> SEQ ID NO 96
<211> LENGTH: 381
<212> TYPE: DNA
<213> ORGANISM: artificial sequence
<220> FEATURE:
<223> OTHER INFORMATION: DNA of 13# nanobody

<400> SEQUENCE: 96
gatgtgcagc tgcaggagtc tggaggaggc tcggtgcagg ctggagggtc tctgagactc      60
tcctgtgcag cctctagatt tacctacagt tggtactgca tgggctggtt ccgccaggct     120
ccggggaagg agcgcgaggg ggtcgcagct atttgcacga caccgagccg cacatacgct     180
gccgactccg tgaagggtcg attcaccatc tccctagaca tcgccaagaa gacgctgtct     240
ctgcaaatgg acagcctgaa atctgaggac actgccatgt actactgtgc ggcagataca     300
agaggagcta tagggttctt caagggcagt gggcccgcca tccctactg gggccagggg      360 acccaggtca ccgtctcctc a                                               381
```

B7-H3 NANOBODY, PREPARATION METHOD AND USE THEREOF

CROSS-REFERENCE TO RELATED APPLICATIONS

The present application is based on PCT filing PCT/CN2020/119893, filed Oct. 9, 2020, which claims priority to Chinese Patent Applications No. 201910953967.4, filed on Oct. 9, 2019, the entire contents of each are incorporated herein by reference.

TECHNICAL FIELD

The present invention relates to a nanobody against the antigenic epitope of a B7-H3 polypeptide molecule, a preparation method and use thereof.

BACKGROUND

B7-H3 (also known as CD276), a member of the B7 family, with the sequence similar to the extracellular domain of PD-L1 (B7-H1), is a phylogenetically conserved protein with various biological functions. B7-H3 is a type I transmembrane protein whose extracellular domain in mice consists of a pair of immunoglobulin variable domain (IgV) and immunoglobulin constant domain (IgC) (2IgB7-H3 isoform); in humans, it consists of two pairs of identical immunoglobulins produced by exon duplication (4IgB7-H3 isoform), which isoform is the predominant isoform expressed. B7-H3 is widely expressed at the mRNA level and can be detected in non-lymphoid organs such as liver, heart, prostate, and lymphoid organs such as spleen and thymus, however, its protein expression is strictly regulated. B7-H3 is structurally expressed on non-immune quiescent fibroblasts, endothelial cells, osteoblasts and amniotic fluid stem cells. After induction, B7-H3 can be expressed on immune cells, especially on antigen-presenting cells. Being co-cultured with regulatory T cells (Treg), dendritic cells can be induced to express B7-H3 protein with IFN-γ, lipopolysaccharide (LPS) or anti-CD40 stimulation in vitro. In addition, B7-H3 expression level can be up-regulated after monocytes and monocyte-derived DCs are stimulated by LPS or differentiated as induced by cytokines, respectively; B7-H3 protein can also be detected on NK cells, B cells, and a small number of T cells after PMA/Ionomycin stimulation. Unlike restricted regulation in normal cells, B7-H3 is abnormally overexpressed in a variety of malignancies, including melanoma, leukemia, breast, prostate, ovarian, pancreatic, rectal and other cancers. High expression of B7-113 is also associated with poor prognosis and poor clinical efficacy, and the development of antibody drugs targeting B7-H3 has become a promising tumor treatment strategy.

Nanobody technology is an antibody engineering revolution led by biomedical scientists on the basis of traditional antibodies by using molecular biology technology combined with the concept of nanoparticle sciences to develop the latest and smallest antibody molecules. It was originally found in camel blood by Belgian scientist Hamers, R. Ordinary antibody proteins are composed of two heavy chains and two light chains, while the nanoantibodies found in camel blood only have two heavy chains. Like traditional antibodies, these "heavy chain antibodies" can bind tightly to targets such as antigens, meanwhile, unlike single-chain antibodies, they are of a low aggregate tendency. Nanobody based on such "heavy chain antibody" is advantageous not only in a molecular weight that is only 1/10 of that of traditional antibodies, but also in its more flexible chemical properties, good stability, high solubility, easy expression, high tumor tissue penetration and easy coupling to other molecules. Therefore, the application of nanobody technology to develop therapeutic antibodies against B7-H3 has great prospects.

SUMMARY OF THE INVENTION

In view of the above problems, on the one hand, the present invention provides a B7-H3 nanobody, which comprises framework regions (FR) and complementarity determining regions (CDR), the complementarity determining regions comprise a complementarity determining region 1 (CDR1), a complementarity determining region 2 (CDR2) and complementarity determining region 3 (CDR3), wherein, the sequence of the complementarity determining region 1 (CDR1) is selected from any one of SEQ ID NO:5, SEQ ID NO:12, SEQ ID NO:19, SEQ ID NO:24, SEQ ID NO:29, SEQ ID NO:34, SEQ ID NO:41, SEQ ID NO:46, SEQ ID NO:51, SEQ ID NO:58, SEQ ID NO:63 and SEQ ID NO:68;

the sequence of the complementarity determining region 2 (CDR2) is selected from any one of SEQ ID NO:6, SEQ ID NO:13, SEQ ID NO:20, SEQ ID NO:25, SEQ ID NO:30, SEQ ID NO:35, SEQ ID NO:42, SEQ ID NO:47, SEQ ID NO:52, SEQ ID NO:59, SEQ ID NO:64, and SEQ ID NO:69; and the sequence of the complementarity determining region 3 (CDR3) is selected from any one of SEQ ID NO:7, SEQ ID NO:14, SEQ ID NO:21, SEQ ID NO:26, SEQ ID NO:31, SEQ ID NO:36, SEQ ID NO:37, SEQ ID NO:43, SEQ ID NO:48, SEQ ID NO:53, SEQ ID NO:60, SEQ ID NO:65, and SEQ ID NO:70.

In one embodiment, the B7-H3 nanobody comprises the following regions in order: a framework region 1 (FR1), a complementarity determining region 1 (CDR1), a framework region 2 (FR2), a complementarity determining region 2 (CDR2), a framework region 3 (FR3), a complementarity determining region 3 (CDR3) and a framework region 4 (FR4), wherein the sequence of the framework region 1 (FR1) is selected from any one of SEQ ID NO:1, SEQ ID NO:8, SEQ ID NO:15, SEQ ID NO:22, SEQ ID NO:27, SEQ ID NO:32, SEQ ID NO: 38, SEQ ID NO:44, SEQ ID NO:49, SEQ ID NO:54, SEQ ID NO:61 and SEQ ID NO:66;

the sequence of the complementarity determining region 1 (CDR1) is selected from any one of SEQ ID NO:5, SEQ ID NO:12, SEQ ID NO:19, SEQ ID NO:24, SEQ ID NO:29, SEQ ID NO:34, SEQ ID NO:41, SEQ ID NO:46, SEQ ID NO:51, SEQ ID NO:58, SEQ ID NO:63 and SEQ ID NO:68;

the sequence of the framework region 2 (FR2) is any one selected from any one of SEQ ID NO:2, SEQ ID NO:9, SEQ 10 NO:16, SEQ ID NO:39, and SEQ ID NO:55;

the sequence of the complementarity determining region 2 (CDR2) is selected from any one of SEQ ID NO:6, SEQ ID NO:13, SEQ ID NO:20, SEQ ID NO:25, SEQ ID NO:30, SEQ ID NO:35, SEQ ID NO:42, SEQ ID NO:47, SEQ ID NO:52, SEQ ID NO:59, SEQ ID NO:64 and SEQ ID NO:69;

the sequence of the framework region 3 (FR3) is selected from any one of SEQ ID NO:3, SEQ ID NO:10, SEQ ID NO:17, SEQ ID NO:23, SEQ ID NO:28, SEQ ID NO:33, SEQ ID NO: 40, SEQ ID NO:45, SEQ ID NO:50, SEQ ID NO:56, SEQ ID NO:62 and SEQ ID NO:67;

the sequence of the complementarity determining region 3 (CDR3) is selected from any one of SEQ ID NO:7, SEQ ID NO:14, SEQ ID NO:21, SEQ ID NO:26, SEQ ID NO:31, SEQ ID NO:36, SEQ ID NO:37, SEQ ID NO:43, SEQ ID NO:48, SEQ ID NO:53, SEQ ID NO:60, SEQ ID NO:65, and SEQ ID NO:70; and the sequence of the framework region 4 (FR4) is selected from any one of SEQ ID NO:4, SEQ ID NO:11, SEQ ID NO:18 and SEQ ID NO:57.

In one embodiment, the B7-H3 nanobody comprises a complementarity determining region 1 (CDR1), a complementarity determining region 2 (CDR2) and a complementarity determining region 3 (CDR3), wherein, the sequence of the complementarity determining region 1 (CDR1) is SEQ ID NO: 5, the sequence of the complementarity determining region 2 (CDR2) is SEQ ID NO: 6, the sequence of the complementarity determining region 3 (CDR3) is SEQ ID NO:7.

In one embodiment, the B7-H3 nanobody comprises a complementarity determining region 1 (CDR1), a complementarity determining region 2 (CDR2) and a complementarity determining region 3 (CDR3), wherein, the sequence of the complementarity determining region 1 (CDR1) is SEQ ID NO: 12, the sequence of the complementarity determining region 2 (CDR2) is SEQ ID NO: 13, the sequence of the complementarity determining region 3 (CDR3) is SEQ ID NO:14.

In one embodiment, the B7-13 nanobody comprises a complementarity determining region 1 (CDR1), a complementarity determining region 2 (CDR2) and a complementarity determining region 3 (CDR3), wherein, the sequence of the complementarity determining region 1 (CDR1) is SEQ ID NO: 19, the sequence of the complementarity determining region 2 (CDR2) is SEQ ID NO: 20, the sequence of the complementarity determining region 3 (CDR3) is SEQ ID NO:21.

In one embodiment, the B7-H3 nanobody comprises a complementarity determining region 1 (CDR1), a complementarity determining region 2 (CDR2) and a complementarity determining region 3 (CDR3), wherein, the sequence of the complementarity determining region 1 (CDR1) is SEQ ID NO: 24, the sequence of the complementarity determining region 2 (CDR2) is SEQ ID NO: 25, the sequence of the complementarity determining region 3 (CDR3) is SEQ ID NO:26.

In one embodiment, the B7-H3 nanobody comprises a complementarity determining region 1 (CDR1), a complementarity determining region 2 (CDR2) and a complementarity determining region 3 (CDR3), wherein, the sequence of the complementarity determining region 1 (CDR1) is SEQ ID NO: 29, the sequence of the complementarity determining region 2 (CDR2) is SEQ ID NO: 30, the sequence of the complementarity determining region 3 (CDR3) is SEQ ID NO:31.

In one embodiment, the B7-H3 nanobody comprises a complementarity determining region 1 (CDR1), a complementarity determining region 2 (CDR2) and a complementarity determining region 3 (CDR3), wherein, the sequence of the complementarity determining region 1 (CDR1) is SEQ ID NO: 34, the sequence of the complementarity determining region 2 (CDR2) is SEQ ID NO: 35, the sequence of the complementarity determining region 3 (CDR3) is SEQ ID NO:36.

In one embodiment, the B7-H3 nanobody comprises a complementarity determining region 1 (CDR1), a complementarity determining region 2 (CDR2) and a complementarity determining region 3 (CDR3), wherein, the sequence of the complementarity determining region 1 (CDR1) is SEQ ID NO: 12, the sequence of the complementarity determining region 2 (CDR2) is SEQ ID NO: 13, the sequence of the complementarity determining region 3 (CDR3) is SEQ ID NO:37.

In one embodiment, the 67-H3 nanobody comprises a complementarity determining region 1 (CDR1), a complementarity determining region 2 (CDR2) and a complementarity determining region 3 (CDR3), wherein, the sequence of the complementarity determining region 1 (CDR1) is SEQ ID NO: 41, the sequence of the complementarity determining region 2 (CDR2) is SEQ ID NO: 42, the sequence of the complementarity determining region 3 (CDR3) is SEQ ID NO:43.

In one embodiment, the B7-H3 nanobody comprises a complementarity determining region 1 (CDR1), a complementarity determining region 2 (CDR2) and a complementarity determining region 3 (CDR3), wherein, the sequence of the complementarity determining region 1 (CDR1) is SEQ ID NO: 46, the sequence of the complementarity determining region 2 (CDR2) is SEQ ID NO: 47, the sequence of the complementarity determining region 3 (CDR3) is SEQ ID NO: 48.

In one embodiment, the B7-H3 nanobody comprises a complementarity determining region 1 (CDR1), a complementarity determining region 2 (CDR2) and a complementarity determining region 3 (CDR3), wherein, the sequence of the complementarity determining region 1 (CDR1) is SEQ ID NO: 51, the sequence of the complementarity determining region 2 (CDR2) is SEQ ID NO: 52, the sequence of the complementarity determining region 3 (CDR3) is SEQ ID NO: 53.

In one embodiment, the 67-H3 nanobody comprises a complementarity determining region 1 (CDR1), a complementarity determining region 2 (CDR2) and a complementarity determining region 3 (CDR3), wherein, the sequence of the complementarity determining region 1 (CDR1) is SEQ ID NO: 58, the sequence of the complementarity determining region 2 (CDR2) is SEQ ID NO: 59, the sequence of the complementarity determining region 3 (CDR3) is SEQ ID NO: 60.

In one embodiment, the B7-H3 nanobody comprises a complementarity determining region 1 (CDR1), a complementarity determining region 2 (CDR2) and a complementarity determining region 3 (CDR3), wherein, the sequence of the complementarity determining region 1 (CDR1) is SEQ ID NO: 63, the sequence of the complementarity determining region 2 (CDR2) is SEQ ID NO: 64, the sequence of the complementarity determining region 3 (CDR3) is SEQ ID NO: 65.

In one embodiment, the B7-H3 nanobody comprises a complementarity determining region 1 (CDR1), a complementarity determining region 2 (CDR2) and a complementarity determining region 3 (CDR3), wherein, the sequence of the complementarity determining region 1 (CDR1) is SEQ ID NO: 68,
the sequence of the complementarity determining region 2 (CDR2) is SEQ ID NO: 69,
the sequence of the complementarity determining region 3 (CDR3) is SEQ ID NO:70.

In one embodiment, the B7-H3 nanobody has an amino acid sequence selected from any one of the following:
SEQ ID NO:71, SEQ ID NO:72, SEQ ID NO:73, SEQ ID NO:74, SEQ ID NO:75, SEQ ID NO:76, SEQ ID NO:77, SEQ ID NO:78, SEQ ID NO:79, SEQ ID NO:80, SEQ ID NO:81, SEQ ID NO:82 and SEQ ID NO:83.

In another aspect, the present invention provides a method for preparing the above B7-H3 nanobody, comprising the following steps:
1). Constructing B7-H3 molecular nanobody library;
2). Screening B7-H3 nanobodies;
3). Detecting single positive clones by immunoblotting;
4). Further verifying positive clones with phage Elisa; and
5). Expressing B7-H3 nanobodies in eukaryotic expression system and purifying them.

In another aspect, the present invention provides a DNA molecule encoding the above-mentioned B7-H3 nanobody.

In yet another aspect, the present invention provides an expression vector comprising the above-mentioned DNA molecule.

In yet another aspect, the present invention provides the use of the above-mentioned B7-H3 nanobody in the preparation of a B7-H3 molecule detection reagent.

In another aspect, the present invention provides the use of the above-mentioned B7-H3 nanobody in the preparation of a medicament for the treatment of malignant tumors with high expression level of B7-H3 molecule.

Technical Effects of the Present Invention

The B7-H3 nanobody of the present invention can specifically bind to B7-H3, therefore, can be used to detect B7-H3 molecules with high sensitivity, and is expected to be used as a therapeutic antibody for the treatment of various malignant tumors with high expression level of B7-H3 molecule.

DETAILED EMBODIMENTS

Figure 1:
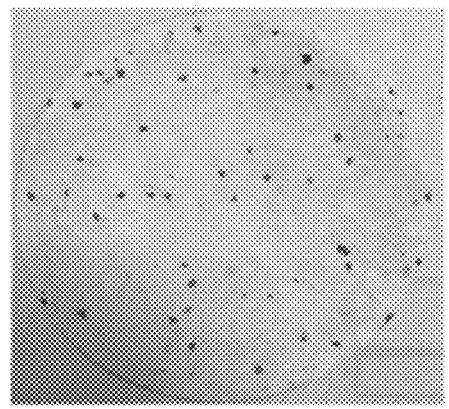
FIG. 1 shows an output phage immunoblot in Example 3.
Figure 2:
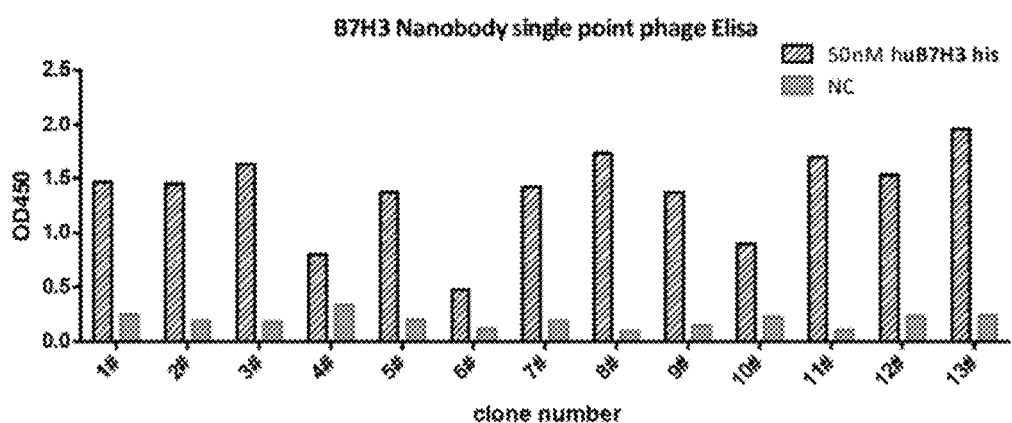
FIG. 2 shows the results of further verification of positive clones with phage Elisa in Example 4.
Figure 3:
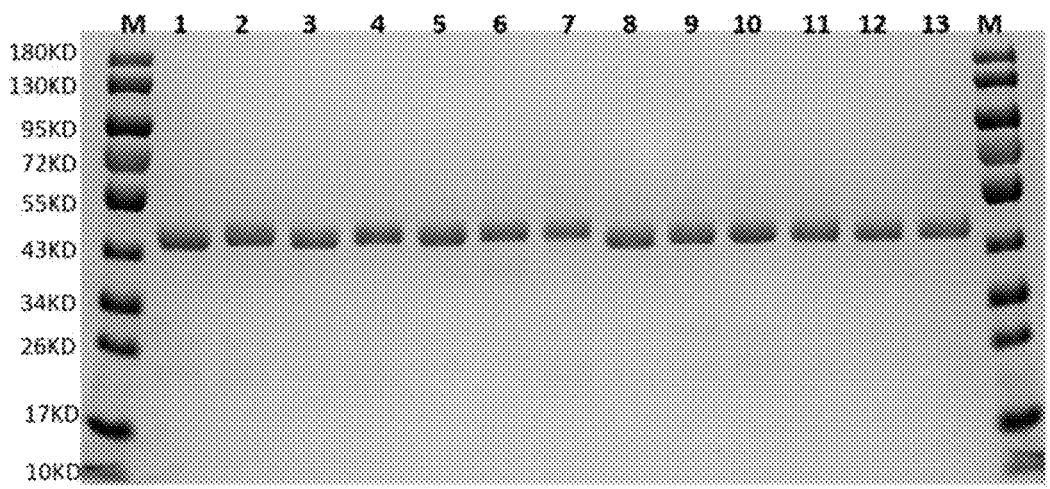
FIG. 3 is the SDS-PAGE picture of the purified 1-13 #nanobodies in Example 5.

The specific preparation process of the nanobodies of the present application will be described below with reference to specific examples. However, those skilled in the art should understand that the scope of the present application is not intended to be limited by these examples, but includes various equivalent and modified forms made by those skilled in the art.

Complete/incomplete Freund's adjuvant (sigma, F5506), streptavidin beads (invitrogen, 65002), casein (Thermo, 37528), PROTRAN BA 85 (Whatman, 10401116), microtiter plate (greiner, 650061)), goat anti-M13HRP (GE, 279421).

Example 1: Construction of Nanobody Library Against B7-H3 Molecular (1) 1 mg of the hu4IgB7-H3 antigen produced by protein expression was mixed with complete Freund's adjuvant in an equal volume and a Xinjiang dromedary was immunized therewith;
(2) Starting from the second week, the dromedary was immunized for 7 times with a mixture of 1 mg of the hu4IgB7-H3 antigen and incomplete Freund's adjuvant in an equal volume to stimulate B cells to express antigen-specific nanobodies;
(3) After 7 immunizations, 100 ml of the peripheral blood lymphocytes of dromedary was collected for extracting total RNA;
(4) cDNA was obtained by Reverse transcription and amplified by nested PCR to obtain VHH fragments;
(5) VHH single-stranded DNA was annealed into the phage vector using the kunkel reaction;
(6) The kunkel product was transformed into electrotransformation competent DH108, and the B7-H3 nanobody library was constructed and the library size was determined. The library size was 1.07×10e9.

Example 2: Screening Nanobodies Against B7-H3

(1) Liquid phase panning:
1. 10e12pfu input phage was blocked with a final concentration of 0.5% casein blocking buffer and incubated for 1 h at room temperature;
2. At the same time, 100 μl streptavidin magnetic beads were washed three times with sterile PBS, the supernatant was discarded, and the resultant was blocked with 500 μl of 1% casein blocking buffer for 1 hour at room temperature;
3. The blocking solution in step 2 was discarded, 1 ml of the blocked phage was added to the magnetic beads, mixed well, rotated and mixed for 15 minutes to allow binding; (negative screening)
4. The supernatant was added into a new sterile EP tube, hu4IgB7-H3-biotin antigen with a final concentration of 100 nM was added thereto, and the resultant was rotated and mixed at room temperature for 2 h to perform binding;
5. At the same time, 100 μl streptavidin magnetic beads were washed three times with sterile PBS, the supernatant was discarded, and the resultant was blocked with 500 lp of 1% casein blocking buffer for 1 h at room temperature;
6. The blocking solution in step 5 was discarded, 1 ml of the phage-hu hu4IgB7-H3-biotin mixture was added to the magnetic beads, mixed well, rotated and mixed for 15 minutes to perform binding;
7. The supernatant was discarded and the magnetic beads were washed 10 times with 1×PBS, and collected;
8. 400 μl of freshly prepared elution buffer containing 100 mM Triethylamine was added to the magnetic beads obtained in step 7, rotated and eluted for 10 min;
9. 400 μl of the supernatant was transferred to a sterile EP tube, 200 μl of pH6.4 Tris-HCl was added for neutralization, after the screening, the output phage was obtained.

(2) Solid phase panning:
1. An immunotube was coated with 1 ml of 100 nM hu-hu4IgB7-H3 antigen solution, and incubated at 4° C. overnight;
2. The next day, the uncoated immune tube was rinsed with 1×PBS for 3 times, spun dry, and blocked with 4 ml of 1% casein blocking buffer with rotation at room temperature for 1 h;
3. 5×10e12 pfu first-round input phage was blocked with a final concentration of 1% BSA, supplemented with 1×PBS to a final volume of 1 ml, and rotated at room temperature for 1 h for blocking;
4. The blocking solution in the antigen-uncoated immunotube was discarded, the blocked phage was put into an antigen-uncoated immunotube, rotated for 2 h for binding (negative screening);
5. At the same time, the coating solution in the antigen-coated immunotube was discarded, and the resultant was rinsed three times with 1×PBS, spun dry, and blocked with 4 ml of blocking buffer with rotation at room temperature for 1 hour;
6. The blocking solution in the antigen-coated immunotube was discarded, and the negatively screened phage was transferred to the immunotube, and rotated for 2 h for binding;
7. After discarding the supernatant, the immunotube was rinsed 10 times with 1×PBST, and spun dry;
8. 1 ml of freshly prepared elution buffer containing 100 mM Triethylamine was added to the immunotube and incubated at room temperature for 10 min;
9. 1 ml of eluate was transferred to a sterile EP tube, and neutralized with 500 μl pH6.4 Tris-HCl. After the screening, output phage was obtained.

Example 3: Detection of Single Positive Clones by Immunoblotting (Mccafferty J, Griffiths A D, Winter G, et al. Phage Antibodies: Filamentous Phage Displaying Antibody Variable Domains[J]. Nature, 1990, 348(6301):552-554. Huse W, Sastry L, Iverson S, et al. Generation of a Large Combinatorial Library of the Immunoglobulin Repertoire in Phage Lambda[J]. Biotechnology, 1989, 246(4935):1275-1281.)

(1) 2000pfu output phage was plated on each LB plate and incubated at 37° C. for 6-8 h;
(2) Whatman 0.45 μm NC membrane was coated with 5 ml of 2 μg/ml anti-M13 antibody and incubated at room temperature for 25 h;
(3) The coating solution was discarded, the NC membrane was blocked with 5 ml of 1% casein blocking buffer, and incubated at room temperature for 1 h;
(4) The blocking solution was discarded, and the NC membrane was washed three times with 1×PBS, and dried in air;
(5) The NC membrane was attached on the LB plate grown with phage, punched holes for positioning, and incubated at room temperature overnight;
(6) The next day, the membrane was removed and placed in a new petri dish, washed 3 times with 1×PBS, and incubated in 100 nM hu4IgB7-H3-biotin for 1 h at room temperature;
(7) The membrane was washed 8 times with 0.1% PBST, added with 1:1000 diluted Neutravidin-AP and incubated at room temperature for 30 min;
(8) The membrane was washed 8 times with 0.1% PBST, added with 10 ml AP chromogenic substrate (100 μl BCIP+100 μl NBT), and developed color at room temperature for 10-30 min;
(9) The positive clones were picked out for plaque PCR and sequencing;
(10) The Sequences were aligned using DNAman sequence alignment software, and clones with the same CDR1, CDR2, and CDR3 were considered as the same clone.

Example 4: Further Verification of Positive Clones with Phage ELISA (1) Amplification of phage: XL1blue $E.$ $coli$ was seeded at 1:100 in LB liquid medium (containing 10 μg/ml tetracycline), grown to OD60=0.6; XI1blue were transferred into 96-well deep-well plates, 600 μl/well, added with 15 μl of the picked phage elution for amplification overnight. The resultant was centrifuged at 4000 rpm for 30 min, and the supernatant was used for phage Elisa;
(2) Elisa detection:
1. The hu4IgB7-H3 antigen was diluted with 1×PBS to 100 nM, the ELISA plate was coated with 50 μl of the diluted solution per well, and incubated overnight at 4'C;
2. After discarding the coating solution, the ELISA plate was spun dry, and rinsed 3 times with 1×PBS;
3. 200 μl of 1% casein blocking buffer was added to each well for blocking at room temperature for 1 hour;
4. After discarding the blocking solution, each well was added with 50 μl of high-titer phage, and incubated at room temperature for 2 hours;
5. The ELISA plate was rinsed 6 times with 0.1% PBST and spun dry;
6. 1:5000 diluted goat anti-M13-HRP antibody was added at 50 μl/well, and incubated at room temperature for 1 h. The plate was washed 6 times with 0.1% PBST and spun dry;
7. 50 μl of TMB color developing solution was added to each well for developing color at room temperature for 5 minutes. 50 μl of 2M $H_2SO_4$ was added to stop the reaction, and the OD450 value was read;
8. The sample wells having OD values 3 times greater than the control well were regarded as positive clones, and 13 positive clones were finally obtained. (The DNA sequences of the 13 nanobodies obtained are SEQ ID No.: 84-96, respectively.)

Example 5: Expression of the Nanobodies in Eukaryotic Expression System and Purification Thereof (1) The VHH fragments of different clones obtained by the previous sequencing analysis were cloned into the PINfuse eukaryotic expression vector;
(2) After sequencing and verifying, the plasmid was extracted;
(3) HEK293F suspension cells were cultured in Freestyle 293 expression medium, when the density reached 1×10e6/ml, and the survival rate was >90%, they were ready for transfection;
(4) The mass ratio of PEI:plasmid was 3:1, and transfection was carried out at the ratio of 1 μg plasmid/1 ml HEK293F cells;
(5) On the 5th-6th day after transfection, cell supernatant was collected, purified with proteinA strain to obtain high-purity antibody protein, and the elution buffer was replaced with PBS using an ultrafiltration column. (The amino acid sequences of the 13 nanobodies obtained are SEQ ID No.: 71-83, respectively.)

The invention claimed is:

1. A B7-H3 a single domain antibody, which comprises framework regions (FR) and complementarity determining regions (CDR), the complementarity determining regions comprise a complementarity determining region 1 (CDR1), a complementarity determining region 2 (CDR2) and complementarity determining region 3 (CDR3), wherein, the sequence of the complementarity determining region 1 (CDR1) is SEQ ID NO: 5,
the sequence of the complementarity determining region 2 (CDR2) is SEQ ID NO: 6,
the sequence of the complementarity determining region 3 (CDR3) is SEQ ID NO:7;
or
the sequence of the complementarity determining region 1 (CDR1) is SEQ ID NO: 12,
the sequence of the complementarity determining region 2 (CDR2) is SEQ ID NO: 13,
the sequence of the complementarity determining region 3 (CDR3) is SEQ ID NO:14;
or
the sequence of the complementarity determining region 1 (CDR1) is SEQ ID NO: 19,
the sequence of the complementarity determining region 2 (CDR2) is SEQ ID NO: 20,
the sequence of the complementarity determining region 3 (CDR3) is SEQ ID NO:21;
or
the sequence of the complementarity determining region 1 (CDR1) is SEQ ID NO: 24,
the sequence of the complementarity determining region 2 (CDR2) is SEQ ID NO: 25,
the sequence of the complementarity determining region 3 (CDR3) is SEQ ID NO:26;
or
the sequence of the complementarity determining region 1 (CDR1) is SEQ ID NO: 29,
the sequence of the complementarity determining region 2 (CDR2) is SEQ ID NO: 30,
the sequence of the complementarity determining region 3 (CDR3) is SEQ ID NO:31;
or
the sequence of the complementarity determining region 1 (CDR1) is SEQ ID NO: 34,
the sequence of the complementarity determining region 2 (CDR2) is SEQ ID NO: 35,
the sequence of the complementarity determining region 3 (CDR3) is SEQ ID NO:36;
or
the sequence of the complementarity determining region 1 (CDR1) is SEQ ID NO: 12,
the sequence of the complementarity determining region 2 (CDR2) is SEQ ID NO: 13,
the sequence of the complementarity determining region 3 (CDR3) is SEQ ID NO:37;
or
the sequence of the complementarity determining region 1 (CDR1) is SEQ ID NO: 41,
the sequence of the complementarity determining region 2 (CDR2) is SEQ ID NO: 42,
the sequence of the complementarity determining region 3 (CDR3) is SEQ ID NO:43;

or
the sequence of the complementarity determining region 1 (CDR1) is SEQ ID NO: 46,
the sequence of the complementarity determining region 2 (CDR2) is SEQ ID NO: 47,
the sequence of the complementarity determining region 3 (CDR3) is SEQ ID NO: 48;
or
the sequence of the complementarity determining region 1 (CDR1) is SEQ ID NO: 51,
the sequence of the complementarity determining region 2 (CDR2) is SEQ ID NO: 52,
the sequence of the complementarity determining region 3 (CDR3) is SEQ ID NO: 53;
or
the sequence of the complementarity determining region 1 (CDR1) is SEQ ID NO: 58,
the sequence of the complementarity determining region 2 (CDR2) is SEQ ID NO: 59,
the sequence of the complementarity determining region 3 (CDR3) is SEQ ID NO: 60;
or
the sequence of the complementarity determining region 1 (CDR1) is SEQ ID NO: 63,
the sequence of the complementarity determining region 2 (CDR2) is SEQ ID NO: 64,
the sequence of the complementarity determining region 3 (CDR3) is SEQ ID NO: 65;
or
the sequence of the complementarity determining region 1 (CDR1) is SEQ ID NO: 68,
the sequence of the complementarity determining region 2 (CDR2) is SEQ ID NO: 69,
the sequence of the complementarity determining region 3 (CDR3) is SEQ ID NO:70.

2. The B7-H3 a single domain antibody according to claim 1, wherein, the B7-H3 a single domain antibody has an amino acid sequence selected from any one of the following:
SEQ ID NO:71, SEQ ID NO:72, SEQ ID NO:73, SEQ ID NO:74, SEQ ID NO:75, SEQ ID NO: 76, SEQ ID NO:77, SEQ ID NO:78, SEQ ID NO:79, SEQ ID NO:80, SEQ ID NO:81, SEQ ID NO:82 and SEQ ID NO:83.

3. A DNA molecule encoding the B7-H3 a single domain antibody of claim 1.

4. An expression vector comprising the DNA molecule of claim 3.

5. A method of preparing a B7-H3 molecule detection reagent using the B7-H3 a single domain antibody of claim 1.

6. A DNA molecule encoding the B7-H3 a single domain antibody of claim 2.

7. A method of preparing a B7-H3 molecule detection reagent using the B7-H3 a single domain antibody of claim 2.

* * * * *